(12) United States Patent
Kohani

(10) Patent No.: US 7,273,370 B2
(45) Date of Patent: Sep. 25, 2007

(54) DEVICE AND METHOD FOR VACUUM ASSISTED DENTAL IMPRESSION

(75) Inventor: Kambiz Kohani, Carlsbad, CA (US)

(73) Assignee: Joe Dentist, Inc., San Diego, CA (US)

( * ) Notice: Subject to any disclaimer, the term of this patent is extended or adjusted under 35 U.S.C. 154(b) by 213 days.

(21) Appl. No.: 11/015,698

(22) Filed: Dec. 17, 2004

(65) Prior Publication Data

US 2005/0221254 A1    Oct. 6, 2005

Related U.S. Application Data

(60) Provisional application No. 60/532,505, filed on Mar. 31, 2004.

(51) Int. Cl.
*A61C 9/00* (2006.01)

(52) U.S. Cl. ........................................................ 433/37

(58) Field of Classification Search ............. 433/36–48
See application file for complete search history.

(56) References Cited

U.S. PATENT DOCUMENTS

| | | | | |
|---|---|---|---|---|
| 3,056,205 A | * | 10/1962 | Ennor | 433/35 |
| 3,431,648 A | * | 3/1969 | Kubalek | 433/214 |
| 3,987,545 A | * | 10/1976 | Kennedy | 433/36 |
| 4,368,040 A | * | 1/1983 | Weissman | 433/36 |
| 4,459,107 A | * | 7/1984 | Weissman | 433/36 |
| 5,370,533 A | * | 12/1994 | Bushnell | 433/36 |
| 5,513,986 A | * | 5/1996 | Feltham et al. | 433/91 |
| 6,394,802 B1 | * | 5/2002 | Hahn | 433/37 |

* cited by examiner

*Primary Examiner*—John J Wilson
(74) *Attorney, Agent, or Firm*—Nydegger & Associates

(57) ABSTRACT

A device for forming a mold for a dental prosthetic includes a dental tray that provides connection to a vacuum source. Additionally, the device includes a dam that may be used to selectively block suction from the vacuum source. The method for forming a mold for a dental prosthetic includes forming an impression with a dental tray including a dam and then forming a mold within the impression after portions of the dam are selectively removed to allow suction to draw in moldable material to the desired teeth.

20 Claims, 3 Drawing Sheets

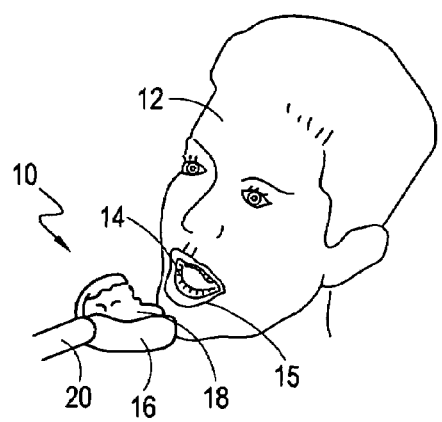
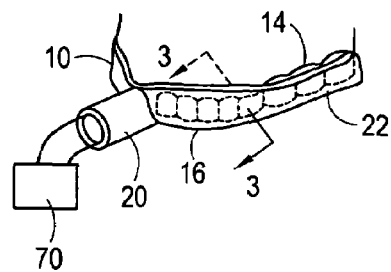
Fig. 1
Fig. 2
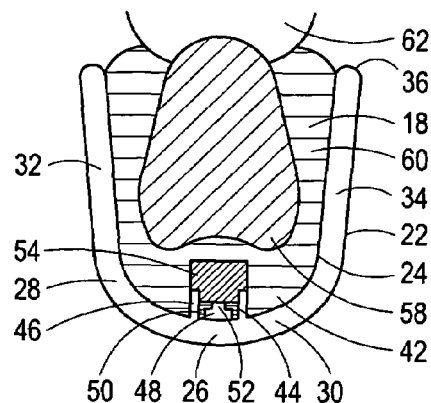
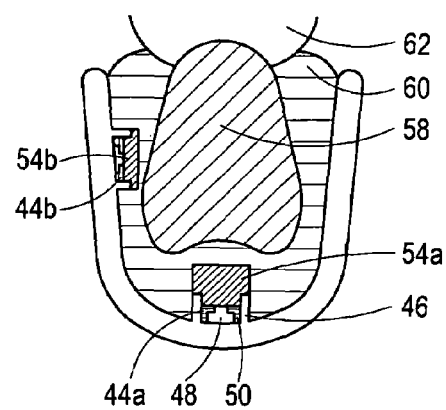
Fig. 3A
Fig. 3B
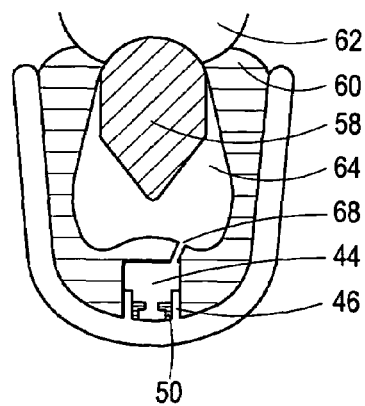
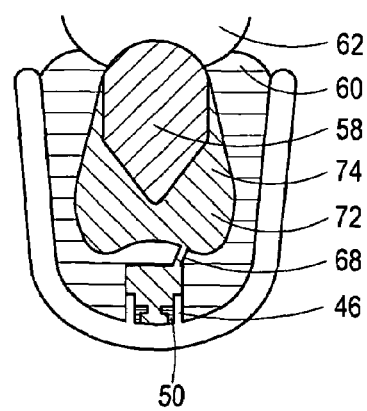
Fig. 3C
Fig. 3D

DEVICE AND METHOD FOR VACUUM ASSISTED DENTAL IMPRESSION This application claims the benefit of U.S. Provisional Patent Application Ser. No. 60/532,505 filed Mar. 31, 2004, the disclosure of which is herein incorporated by reference.

FIELD OF THE INVENTION

The present invention pertains generally to devices and methods for making dental models. More particularly, the present invention pertains to such devices and methods that use suction means to draw a mold-forming material into contact with the teeth within a dental impression tray. The present invention is particularly, but not exclusively, useful for creating a mold of a patient's teeth by selectively providing suction to desired areas in the mouth to draw the mold-forming material into contact with the teeth.

BACKGROUND OF THE INVENTION

In order to make an artificial tooth, crown, or other dental prosthetic, dentists usually require a dental model. Conventionally, such a model is formed by the impression left in a dental impression tray filled with a self-hardening, gum-like compound. To form the impression, the tray is inserted into the patient's mouth and the compound fills in the area around the teeth before hardening. After removing the tray and compound from the mouth, a model material is poured into the dental impression and hardens to form the model of the patient's teeth.

When preparing a crown for a tooth, the tooth is typically prepared by reshaping and reducing its size. This enables the crown to fit over the tooth without disrupting the patient's other teeth. Once the tooth is reshaped, a thin piece of retraction cord is typically placed around it before a dental impression is taken. This impression is used to form the model that the dentist will use when constructing the crown.

As can be imagined, the crown must be formed to fit precisely on the reshaped tooth and between the adjacent teeth. Furthermore, the crown must not obstruct the patient's bite. Therefore, it is vital that the dental impression be accurate so that the proper crown can be prepared. Unfortunately, dental impressions prepared under the currently practiced method often suffer from significant inaccuracies. Some inaccuracies are caused by the movement of the patient's tongue, lips, cheeks or jaw. Other inaccuracies are due to the fact that the impression material tends not to adhere tightly to the teeth since it is designed to be easily removed from the teeth. As a result, the models prepared from these faulty dental impressions share their inaccuracies. More importantly, the crowns or other dental prosthetics formed using the models also include their inaccuracies. In order to overcome this, dentists often must alter the crown when mounting it to the reshaped tooth—a process that can be difficult for both the dentist and the patient.

In light of the above, it is an object of the present invention to provide devices and methods for forming a mold for a dental model having improved accuracy. Another object of the present invention is to provide devices and methods for forming a mold for a dental model that uses suction to draw the moldable material into contact with the teeth. It is yet another object of the present invention to provide devices and methods for forming a dental impression in which an impression of the patient's tooth is taken before a final mold of the reshaped tooth is taken within the impression. Another object of the present invention is to provide dental impression devices and methods that allow for selective suctioning of moldable material within the patient's mouth. Still another object of the present invention is to provide devices for forming dental impressions, and methods of using the devices, that are relatively easy to manufacture, simple to use and comparatively cost effective.

SUMMARY OF THE INVENTION

The present invention is directed to a dental impression device that can be used for forming a mold for a dental prosthetic. Preferably, the impression device comprises a dental tray for use with a vacuum source. Also included is a dam that is engageable with the tray to selectively block suction by the vacuum source within selected areas of the tray.

Structurally, the dental tray includes a generally U-shaped base extending between a labial (lip/cheek) side and a lingual (tongue) side. Connected to the base on its labial side is a generally U-shaped labial wall that extends away from the base. Connected to the base on its lingual side is a generally U-shaped lingual wall that also extends away from the base. When intended to form a mold of maxillary teeth, the tray may further include a palatine member that is connected to the upper edge of the lingual wall to span the void formed by the U-shaped wall. Preferably, the base and walls define the dental tray's outer surface. They also define its inner surface which forms a channel.

In accordance with the present invention, a trough is formed in the base portion of the channel, and this trough includes a series of apertures. A conduit which is in fluid communication with the apertures leads from the trough to a port on the outer surface of the tray. Specifically, the port is connected to the conduit at the outer surface for communication with the vacuum source. Additionally, the dam is positioned in the trough to selectively engage the apertures and interrupt (i.e. block) fluid communication with the vacuum source. If desired, the dam may include multiple dam portions that allow engagement of non-adjacent selected apertures. Further, the preferred dam portions may include projections extending away from the trough.

To form a mold for a dental prosthetic, the dam is positioned in the trough to block the apertures, and a moldable material is placed in the channel of the tray. Then the tray is positioned about the patient's teeth so that the moldable material surrounds the teeth. When the moldable material sets, an intermediate impression of the teeth is formed and the tray is removed. Thereafter, dental work may be performed on the desired tooth. Such work preferably includes the removal of dental matter from the tooth.

Once the dental work is completed, a final mold of the teeth is taken. To create this final mold, selected dam portions are removed from the trough in the tray to unblock selected apertures. Dam portions may be removed by cutting into the intermediate impression. Alternatively, if their projections extend through the intermediate impression, dam portions may be simply grasped at their projections and pulled from the trough. In either case, one or more holes are formed in the intermediate impression when the selected dam portions are removed. Next, another moldable material, preferably with a lower viscosity than the previously used moldable material, is placed in the intermediate impression. Preferably, at least a portion of this moldable material is placed along the upper labial wall side and lingual wall side of the impression. When the tray and intermediate impression are repositioned in the patient's mouth, the moldable material is dragged toward the reshaped tooth through contact with the patient's teeth.

In order to further draw the moldable material into contact with the reshaped tooth, the vacuum source is connected in fluid communication with the unblocked aperture. Specifically, to do this the port is connected to a vacuum source. With this connection, upon activation of the vacuum source, the moldable material is drawn toward the holes in the intermediate impression so that it contacts and molds around the reshaped tooth. After the moldable material sets, the dental tray and final dental mold can be removed from the mouth. This final mold can then be used to prepare crowns or other dental prosthetics.

While the trough disclosed above is located in the base of the dental tray, it may be positioned elsewhere, such as in the labial wall. In addition, multiple troughs and dams may be used to provide increased suction to desired areas in the mouth. For instance, troughs may be provided in the base and in the labial wall with the troughs in communication with a vacuum source or sources.

Additionally, while the moldable material that forms the final mold is disclosed as being less viscous than the moldable material that forms the intermediate impression, it may be more viscous or equally viscous as desired.

Finally, while the discussion above expressly discusses the creation of a crown for a tooth, it is to be understood that use of the present invention is contemplated for formation of any type of dental prosthetic that may be facilitated by use of a dental model.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a perspective view of a patient receiving a dental impression device in accordance with the present invention;

FIG. 2 is a perspective view, with hidden features shown in phantom for clarity, of the dental impression device of FIG. 1 while engaging the patient's teeth in accordance with the present invention;

FIG. 3A is a cross sectional view taken along line 3-3 in FIG. 2 showing the tooth and molding material during the initial molding process with one trough in the channel;

FIG. 3B is a cross sectional view similar to FIG. 3A showing the tooth and molding material during the initial molding process with two troughs in the channel;

FIG. 3C is a cross sectional view of the tooth of FIG. 3A shown after the tooth is reshaped and positioned back in the dental tray;

FIG. 3D is a cross sectional view of the tooth of FIG. 3C shown after a dam portion has been removed from the intermediate dental impression and the molding material has been drawn into contact with the reshaped tooth;

DESCRIPTION OF THE PREFERRED EMBODIMENTS

Figure 3E:
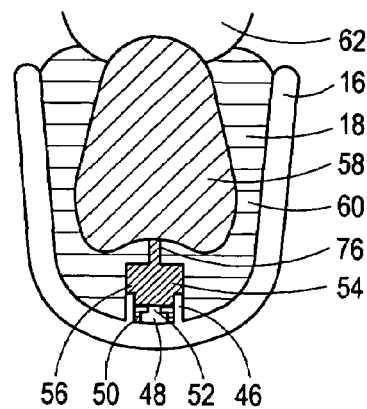
FIG. 3E is a cross sectional view of the tooth of FIG. 3A shown with an alternate dam which has a projection contacting the tooth.

Referring initially to FIGS. 1 and 2, a dental impression device in accordance with the present invention is shown and generally designated 10. As shown in FIG. 1, the dental impression device 10 is received by a patient 12 around the patient's teeth 14. As also shown, the dental impression device 10 includes a dental tray 16. Received within the dental tray 16 is a moldable material 18 which contacts and molds around the patient's teeth 14. Also shown is a port 20 that extends from the outer surface 22 of the dental tray 16.

Figure 4B:
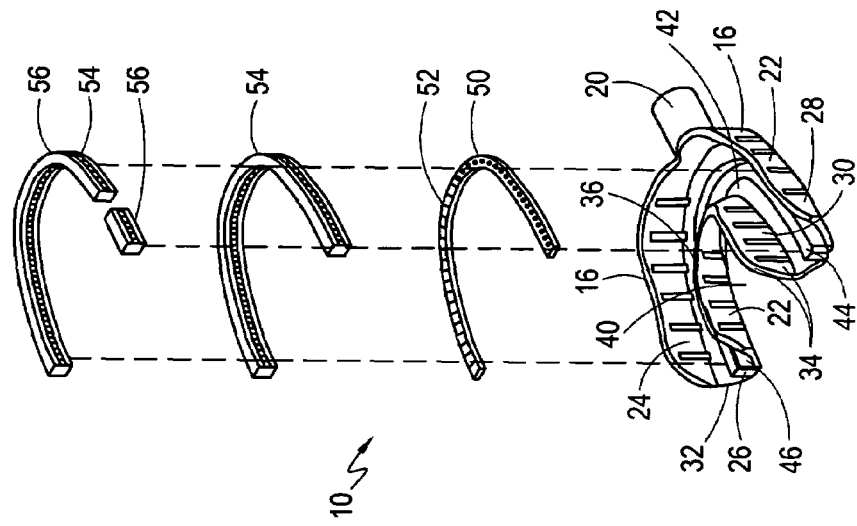
FIG. 4B is an exploded perspective view showing the components of an alternate dental impression device similar to that shown in FIG. 4A.
Figure 4A:
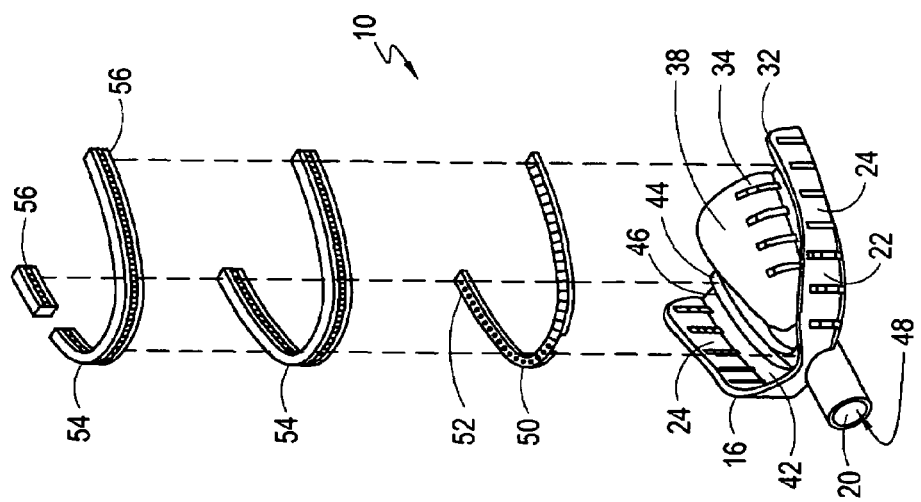
FIG. 4A is an exploded perspective view showing the components of the dental impression device from FIG. 2.

Referring now to FIGS. 4A and 4B, additional features of the dental impression device 10 may be seen. In addition to the outer surface 22, dental tray 16 includes an inner surface 24. As can be seen, these surfaces 22, 24 are formed in part by a U-shaped base 26 that extends from a labial side 28 to a lingual side 30. Extending up from the labial side 28 of base 26 is a U-shaped labial wall 32. Likewise, a U-shaped lingual wall 34 extends up from the lingual side 30 of base 26. As shown in FIG. 4B, the lingual wall 34 ends at an edge 36 when intended for use with mandibular teeth. However, as seen in FIG. 4A, when intended for use with maxillary teeth, a palatine member 38 connects to, and spans the void 40 created by, the lingual wall 34.

Referring still to FIGS. 4A and 4B, it can be seen that the inner surface 24 of the dental tray 16 forms a channel 42 for receiving the patient's teeth 14 and the moldable material 18. The channel 42 includes a trough 44 formed by upright members 46 which are preferably integral with the base 26. At the base of the trough 44 is a conduit 48 that connects the trough 44 to the port 20. Positioned within the trough 44 is a stand 50 that includes apertures 52 which are in fluid communication with the conduit 48. In addition to the dental tray 16, FIGS. 4A and 4B show a dam 54. The dam 54 is positionable within the trough 44 to block the apertures 52. The dam 54 may be comprised of a plurality of dam portions 56 to allow certain apertures 52 to be blocked while other apertures 52 are unblocked.

Referring now to FIG. 3A, the operation of the dental impression device 10 may be understood with respect to a tooth 58 upon which dental work will be done. The tooth 58 is shown received within the channel 42 formed by dental tray 16. In addition to the tooth 58, the channel 42 holds the moldable material 18 that is surrounding the tooth 58. The moldable material 18 is initially a viscous liquid but will harden into a solid dental impression 60, thereby retaining the negative imprint of tooth 58. As shown, the moldable material 18 surrounds the entire tooth 58 and contacts the patient's gums 62.

FIG. 3A also provides a clear view of the components of the dental impression device 10. For instance, the dam 54 is shown blocking an aperture 52 formed by stand 50. Below the aperture 52 is the conduit 48 that leads to the port 20.

An alternate dental tray 16 is shown in FIG. 3B. In this dental tray 16, the channel 42 includes a base trough 44a and a wall trough 44b. As shown, each trough 44a, 44b is blocked by a dam 54a, 54b. Additionally, each trough 44a, 44b includes substantially identical components including a conduit 48 which leads to port 20.

Referring now to FIG. 3C, the tooth 58 is shown after dental work, including reshaping, has been performed on it. As shown, a space 64 exists between the tooth 58 and the impression 60. This space 64 is equal to the volume of dental matter removed from the tooth 58. As seen in FIG. 3C, a portion 56 of the dam 54 has been removed from the dental tray 16. Specifically, the impression 60 has been pierced to create a hole 68 and the dam portion 56 has been pulled out of the trough 44 through the hole 68.

As seen in FIG. 3D, suction by a vacuum source 70 (shown in FIG. 2) has been communicated through the conduit 48 to the space 64 to draw in a moldable material 72. As shown, the moldable material 72 contacts the tooth 58 and impression 60 and has filled in space 64. The moldable material 72 hardens to form a mold 74 that can be utilized to prepare a dental prosthetic such as a crown.

Figure 3F:
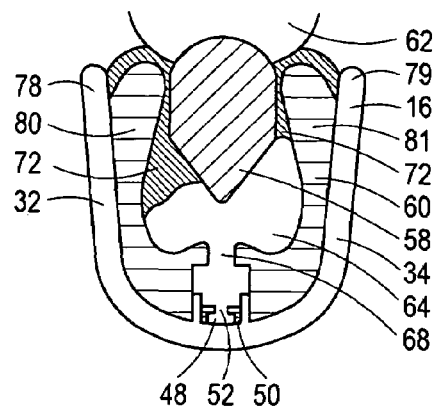
FIG. 3F is a cross sectional view of the tooth of FIG. 3E shown after the selected dam portion has been removed, and after the tooth has been reshaped and positioned back in the dental tray.
Figure 3G:
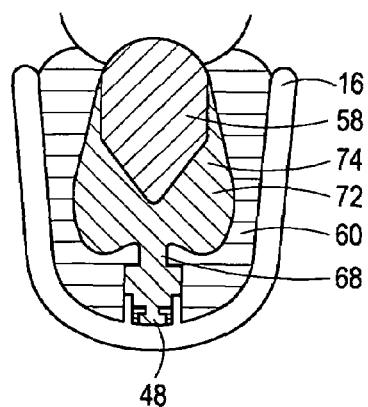
FIG. 3G is a cross sectional view of the tooth of FIG. 3F shown after the molding material has been drawn into contact with the reshaped tooth.

FIGS. 3E-3G show an alternate embodiment of the dam 54 which includes a projection 76. As shown in FIG. 3E, the projection 76 extends through the moldable material 18 during formation of the impression 60 so that it contacts the tooth 58. When the dental tray 16 and impression 60 are removed from the patient's mouth 15, a selected projection 76 can be grasped and pulled to remove the selected dam portion 56 from the trough 44.

As shown in FIG. 3F, removal of the selected dam portion 56 leaves a hole 68 where the projection 76 was formerly positioned. The hole 68 allows the vacuum source 70 to draw moldable material 72 into the space 64 around tooth 58. As shown in FIG. 3F, the moldable material 72 has been positioned on the distal portions 78,79 of the labial wall 32 and lingual wall 34 of the tray 16 and on the distal portions 80,81 of the impression 60 adjacent the labial wall 32 and lingual wall 34 of the tray 16. This allows the moldable material 72 to be dragged toward the space 64 when the tray 16 is positioned around the patient's teeth 14.

After the tray 16 is positioned around the patient's teeth 14, the vacuum source 70 is connected and activated and the moldable material 72 is drawn into contact with the reshaped tooth 58 to form the mold 74. FIG. 3G depicts the mold 74 after this process has been completed. As shown, the moldable material 72 has been fully drawn into the space 64 and has passed through the hole 68 and the aperture 52 into the conduit 48.

While the particular device and method as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A dental impression device for forming a mold for a dental prosthetic, the impression device comprising:
   a dental tray having:
   a generally U-shaped base extending between a lingual wall and a labial wall;
   a base portion communicating between said lingua wall and said labial wall;
   an outer surface;
   an inner surface defined by an area between said lingual wall, said bottom portion, and said labial wall, said inner surface defining a channel for receiving a patient's teeth and a moldable material;
   a trough formed in said base portion of said channel;
   apertures formed within said trough in the channel; and
   a conduit extending from the apertures to a port for connection to a vacuum source for drawing moldable material in the channel toward the apertures; and
   a dam engageable with said trough, said dam providing means to block selected apertures in said trough to limit suction of air from desired portions of the channel to draw the stationary moldable material positioned in said channel, into contact with the patient's tooth.

2. A dental impression device as recited in claim 1 further comprising wherein the apertures communicate through a stand which is engagable within the trough and the dam is positionable in the trough for engagement with the selected apertures.

3. A dental impression device as recited in claim 2 wherein the dam includes multiple dam portions each engagable with said trough as a means to block non-adjacent said selected apertures in said stand.

4. A dental impression device as recited in claim 2 wherein the lingual wall extends to an edge defining a void, and further comprising a palatine member connected to the edge of the lingual wall and spanning the void.

5. A dental impression device as recited in claim 1 wherein the dam includes multiple dam portions each engagable with said trough as a means to block non-adjacent said selected apertures.

6. A dental impression device as recited in claim 1 wherein the lingual wall extends to an edge defining a void, and further comprising a palatine member connected to the edge of the lingual wall and spanning the void.

7. A dental impression device as recited in claim 1 a wherein said trough is formed in the labial wall, and wherein the apertures are formed in the trough and the dam is engageable in the trough for said engagement with said selected apertures.

8. A dental impression device as recited in claim 1 further comprising
   a labial trough formed in the labial wall;
   secondary apertures formed in the labial trough, said secondary apertures communicating with said port; and
   the dam having multiple dam portions, said dam portions possionable in the base trough and in the labial trough for engagement with the selected apertures.

9. A dental impression device for forming a mold for a dental prosthetic, the impression device comprising:
   a dental tray having an outer surface and an inner surface defining a channel for receiving a patient's teeth and a moldable material;
   a trough formed within said channel between a pair of sidewalls communicating with said inner surface;
   a plurality of apertures formed within said trough;
   a suction means engageable with said apertures, said suction means for drawing the moldable material into contact with the patient's teeth;
   means to block at least one of said apertures; and
   said means to block at least one of said apertures providing a means for focusing the suction means on a desired tooth such that the moldable material is drawn into contact with the desired tooth.

10. A dental impression device as recited in claim 9 wherein the means means to block at least one of said apertures includes a dam for blocking the suction means from drawing the moldable material into contact with non-desired teeth.

11. A dental impression device as recited in claim 10 wherein the dam includes multiple dam portions for blocking the suction means from communicating with a plurality of said apertures thereby preventing a drawing of the moldable material into contact with non-adjacent non-desired teeth.

12. A dental impression device as recited in claim 9 wherein the suction means includes apertures formed in a stand positionable within said trough and a conduit extending from the apertures to a port for connection to a vacuum source.

13. A method of forming a mold for a dental prosthetic in a dental tray having a channel for receiving the moldable materials, and a trough within said channel, a stand engageable with said trough having apertures formed in therein, and a conduit extending from the apertures to a port for connection to a vacuum source for drawing the second moldable material into the space, the method comprising:
    putting a first moldable material in the tray;
    positioning the tray about a patient's teeth to form an impression of the teeth with the first moldable material;
    removing the tray from the patient's teeth;
    performing dental work on at least one subject tooth to include removing a selected volume of dental matter from the subject tooth;
    putting a second moldable material in the impression;
    repositioning the tray and the impression with the second moldable material about the patient's teeth, with the impression and the subject tooth defining a space therebetween; and
    creating a vacuum in the space to draw the second moldable material into the space and into contact with the subject tooth to form a mold with the second moldable material for use in shaping the dental prosthetic.

14. A method as recited in claim 13 further comprising:
    blocking the apertures in the channel with a dam by engaging it with said trough during formation of the impression; and
    unblocking at least one selected aperture before the creating step to allow the vacuum source to draw the second moldable material into the space.

15. A method as recited in claim 14 further comprising the step of:
    piercing the impression to form at least one hole to unblock at least one selected aperture and to allow the vacuum source to draw the second moldable material into the space via the hole.

16. A method as recited in claim 14 wherein the dam contacts the subject tooth during formation of the impression and prior to the performing step to form at least one hole in the impression for fluid communication with the vacuum source upon removal of the dam from the tray to allow the vacuum source to draw the second moldable material into the space via the hole.

17. A method as recited in claim 13 wherein the channel includes a trough and the apertures are formed in the trough, the method further comprising the steps of:
    positioning a dam in the trough to block the apertures before putting the first moldable material in the tray; and
    unblocking at least one selected aperture before the drawing step to allow the vacuum source to draw the second moldable material into the space.

18. A method as recited in claim 17 wherein the unblocking step includes removing portions of the dam from the trough through the impression to unblock the selected aperture(s).

19. A method as recited in claim 13 wherein the first moldable material and the second moldable material are comprised of different substances.

20. A method as recited in claim 19 wherein the second moldable material is less viscous than the first moldable material.

* * * * *